United States Patent [19]

Miller et al.

[11] Patent Number: 4,694,081

[45] Date of Patent: Sep. 15, 1987

[54] PROCESS TO PREPARE 2,5-DIKETOPIPERAZINES

[75] Inventors: William H. Miller, Glendale; William D. Taylor, St. Louis, both of Mo.

[73] Assignee: Monsanto Company, St. Louis, Mo.

[21] Appl. No.: 778,817

[22] Filed: Sep. 23, 1985

[51] Int. Cl.$^4$ .......................................... C07D 241/08
[52] U.S. Cl. .................................................. 544/385
[58] Field of Search ......................................... 544/385

[56] References Cited

U.S. PATENT DOCUMENTS

| | | | |
|---|---|---|---|
| 2,913,496 | 11/1959 | Cluff | 544/385 |
| 3,239,528 | 3/1966 | Bebenburg et al. | 544/385 |
| 4,140,791 | 2/1979 | Chan | 544/385 |
| 4,400,330 | 8/1983 | Wong et al. | 544/337 |
| 4,477,666 | 10/1984 | Hori et al. | 544/385 |

OTHER PUBLICATIONS

Sut et al, "N-Monoalkylation of Some 2-Oxo and 2,5-Diketopiperazines", *Chimie Therapeutique*, 4 (3), 167-173 (1969).

Okawara et al, "Convenient Syntheses of Piperazines-2,5-Diones and Lactams from Halocarboxamides Using Phase Transfer Catalysts", Chemistry Letters, 1981, pp. 185-188.

Cavicchioni et al, "Base-Promoted Reactions of α-Halogenoalkylanilides", *J. Chem. Soc. Perkin Trans. I*, pp. 2969-2972 (1982).

Primary Examiner—Glennon H. Hollrah
Assistant Examiner—James H. Turnipseed
Attorney, Agent, or Firm—Frank D. Shearin

[57] ABSTRACT

Substituted and unsubstituted 2,5-diketopiperazines can be prepared by a process which comprises bringing together a substituted or unsubstituted glycinamide and a haloacetyl halide, optionally in the presence of a non-nucleophilic base, and thereafter adding a stronger base.

20 Claims, No Drawings

PROCESS TO PREPARE 2,5-DIKETOPIPERAZINES

BACKGROUND OF THE INVENTION

This invention relates to the synthesis of cyclic peptides, and more particularly to a novel method for the synthesis of substituted and unsubstituted 2,5-diketopiperazines.

2,5-Diketopiperazines are useful as fungicides and as intermediates for the synthesis of other compounds. Thus, for example Chan et al, U.S. Pat. No. 4,140,791 discloses the use of 1,4-di(2,6-dimethylphenyl)-2,5-diketopiperazine for control of various fungal disease. Sut et al "N-Monoalkylation of some 2-Oxo and 2,5-Dioxopiperazines", *Chimie Therapeutique*, 4 (3), pp. 167–173 (1969), describes the synthesis of a series of 2-oxopiperazine and 2,5-dioxopiperazines which were found to have analgesic and anesthetic activities.

The copending and coassigned applications of Miller and Taylor, Ser. No. 778,818 filed Sept. 23, 1985 Miller, Reitz and Pulwer Ser. No. 178,958, filed Sept. 23, 1985 describe the use of 1,4-disubstitued 2,5-diketopiperazines in a synthesis scheme leading to the preparation of N-phosphonomethylglycine. N-phosphonomethylglycine, known also by its common name, glyphosate, is a highly effective and commercially important phytotoxicant useful in controlling a large variety of weeds. It is applied to the foliage of a very broad spectrum of perennial and annual grasses and broadleaf plants. Industrial uses include control of weeds along roadsides, waterways, transmission lines, storage areas, and other non-agricultural areas. Usually glyphosate is formulated into herbicidal compositions, preferably in water. The aforesaid copending application of Miller, Reitz and Pulwer Ser. No. 778,958 describes a method in which an aqueous solution of N-alkyl glyphosate may be prepared without isolation of intermediate by a reaction scheme commencing with N,N'-dialkyl-2,5-diketopiperazine.

Okawara et al, "Convenient Synthesis of Piperazine-2,5-diones and Lactams from Halocarboxamides Using Phase Transfer Catalysts", *Chemistry Letters*, 1981, pp. 185–189, describes the synthesis of various 1,4-disubstituted-2,5-diketopiperazines by intermolecular condensation of halocarboxamides using a reaction system comprising a mixture of dichloromethane and 50% aqueous sodium hydroxide solution in the presence of a solid phase transfer catalyst. Among the compounds whose synthesis are reported by Okawara et al are 1,4-dibenzylpiperazine-2,5-dione, 1,4-diphenylpiperazine-2,5-dione and 1,4-diphenyl-3,6-dimethylpiperazine-2,5-dione. The reference does not report any use for the products synthesized.

Cavicchioni et al, "Base Promoted Reactions of α-Halogeno-alkylanilides," *Chem. Soc. Perkin Trans.* I, pp. 2969–2972 (1982), reports the preparation of both N,N'-dialkylpiperazines and 2-amino-2-halolkyloxazolidones by intermolecular condensations of the same reactants used in the synthesis described by Okawara. Cavicchioni et al do not give much detail on the reaction system utilized but apparently employed a polar organic solvent system rather than a two-phase system comprising a phase transfer catalyst.

Wong et al U.S. Pat. No. 4,400,330 describes the preparation of bis-phosphonomethyl-2,5-diketopiperazine by phosphonomethylation of 2,5-diketopiperazine, followed by hydrolysis of the bis-phosphonomethyl-2,5-diketopiperazine to produce glyphosate. In the phosphonomethylation, formaldehyde and glacial acetic acid are added to 2,5-diketopiperazine to produce a suspension which is refluxed. Thereafter, phosphorus trichloride is added to the reaction mixture which is then maintained at reflux until all hydrogen chloride by-product has been driven off. After additional refluxing of the reaction slurry, the product is dried in vacuo, dissolved in water, and treated sequentially with caustic solution and mineral acid to effect hydrolysis and produce glyphosate.

SUMMARY OF THE INVENTION

Among the several objects of the present invention may be noted the provision of a novel and improved method for the synthesis of substituted or unsubstituted 2,5-diketopiperazines; the provision of such a method which affords both high productivity and high yield; the provision of such a method which can be economically implemented; and in particular provision of such a method which does not require the use of a phase transfer catalyst.

These and other objects are achieved by a process for the preparation of a substituted or unsubstituted 2,5-diketopiperazine represented by the formula:

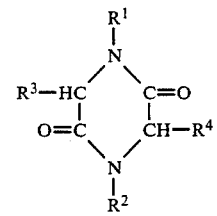

where $R^3$ and $R^4$ are independently selected from the group consisting of hydrogen, alkyl and aryl, and $R^1$ and $R^2$ are independently selected from the group consisting of hydrogen, alkyl having between 1 and about 12 carbon atoms, arylmethyl, aryl,

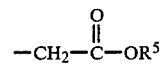

where Y is selected from the group consisting of
—$OR^5$,
—$OR^5$, and

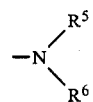

and $R^5$ and $R^6$ are independently selected from the group consisting of alkyl having between 1 and about 6 carbon atoms; the process comprising bringing together under reaction conditions a substituted or unsubstituted glycinamide represented by the formula:

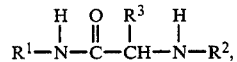

where $R^1$, $R^2$ and $R^3$ are as defined above, and a haloacetyl halide represented by the formula:

$$X^1-\overset{R^4}{\underset{|}{CH}}-\overset{O}{\underset{\|}{C}}-X^2$$

where $X^1$ and $X^2$ are halogen and $R^4$ is as defined above, and in the presence of a base forming said substituted or unsubstituted 2,5-diketopiperazine.

Other objects and features will be in part apparent and in part pointed out hereafter.

DESCRIPTION OF THE PREFERRED EMBODIMENT

In accordance with the invention, it has been found that substituted and unsubstituted 2,5-diketopiperazines can be synthesized in high yield and at high productivity by reaction of a substituted or unsubstituted glycinamide with a haloacetyl halide. Although applicants do not wish to be bound by any particular theory, it is believed that a linear intermediate is formed by condensation of the glycinamide and haloacetyl halide, which can be represented by the following formula:

$$X^1-\overset{R^4}{\underset{|}{CH}}-\overset{O}{\underset{\|}{C}}-\overset{R^2}{\underset{|}{N}}-\overset{R^3}{\underset{|}{CH}}-\overset{O}{\underset{\|}{C}}-NH-R^1$$

where $X^1$, $R^1$, $R^2$, $R^3$ and $R^4$ are as defined above. It is believed that the intermediate undergoes cyclization in the presence of strong base to form the 2,5-diketopiperazine. The process of the invention is economical to implement and is particularly advantageous in avoiding the need for a phase transfer catalyst to promote the progress of the formation of the 2,5-diketopiperazine.

Generally, the glycinamide can be represented by the formula:

$$R^1-\overset{H}{\underset{|}{N}}-\overset{O}{\underset{\|}{C}}-\overset{R^3}{\underset{|}{CH}}-\overset{H}{\underset{|}{N}}-R^2$$

where $R^1$, $R^2$, and $R^3$ are as defined above. Thus, where $R^1$ and/or $R^2$ is an alkyl group, it may typically comprise methyl, ethyl, propyl, isopropyl, n-butyl, sec-butyl, n-pentyl, n-hexyl, 2-ethylhexyl, n-octyl, n-decyl or n-dodecyl. Where $R^1$ and/or $R^2$ is an arylmethyl group, it is typically benzyl, but may also be a substituted benzyl such as nitrobenzyl or sulfonated benzyl. Similarly, where $R^1$ and/or $R^2$ is aryl, it is typically phenyl, but may alternatively be nitrophenyl, sulfonated phenyl, hydroxyphenyl, or carboxyphenyl. As noted, $R^1$ or $R^2$ may also comprise $$-CH_2-\overset{O}{\underset{\|}{C}}-OR^5 \text{ or } Y-CH_2-CH_2-$$

where Y is selected from among
—$OR^5$,
—$SR^5$, $$-N\diagup\overset{R^5}{\diagdown}_{R^6}$$

where $R^5$ and $R^6$ are independently selected from among alkyl groups having between about 1 and about 6 carbon atoms and aryl. Thus, typically, $R^6$ and/or $R^6$ may comprise methyl, ethyl, propyl, isopropyl, n-butyl, sec-butyl, or n-hexyl.

The haloacetyl halide reactant corresponds to the formula:

$$X^1-\overset{R^4}{\underset{|}{CH}}-\overset{O}{\underset{\|}{C}}-X^2$$

where $X^1$ and $X^2$ are both halogen, and $R^4$ is as defined above. Among the specific substituents which can typically comprise $R^3$ or $R^4$ are ethyl, propyl, n-butyl, n-hexyl and phenyl. Preferably, however, $R^3$ and $R^4$ comprise hydrogen, and the haloacetyl halide reactant corresponds to the formula:

$$X^{1'}-CH_2-\overset{O}{\underset{\|}{C}}-X^{2'}$$

where $X^{1'}$ and $X^{2'}$ are independently selected from among chlorine and bromine. Preferably, the haloacetyl halide is chloracetyl chloride.

To carry out the process, the N,N'-disubstituted glycinamide reactant is preferably dissolved in an organic solvent and the haloacetyl halide added slowly, for example drop-wise, to the solution. The solvent utilized comprises an organic solvent which is inert to the haloacetyl halide under the reaction conditions. Most preferably, toluene or xylene is utilized as the reaction solvent.

As noted above, the formation of the 2,5-diketopiperazine must be carried out in the presence of a hydrogen halide scavenger. Although any number of hydrogen halide scavengers are known to those skilled in the art, it is preferred to use a non-nucleophilic base, which is incorporated in the solution containing the substituted or unsubstituted glycinamide prior to addition of the haloacetyl halide. The non-nucleophilic base serves as a hydrogen halide scavenger and in some cases may promote the initial condensation between the substituted or unsubstituted glycinamide and the haloacetyl halide. In general, when a non-nucleophilic base is used, a stronger base is subsequently added to form the desired product.

The initial condensation proceeds rapidly, and substantially quantitatively. Accordingly, the amount of haloacetyl halide charged to the reaction is conveniently and preferably equivalent to the initial glycinamide charge. The non-nucleophilic base is preferably an organic amine such as, for example, triethylamine or pyridine. Alternatively, an excess of the substituted or unsubstituted glycinamide reactant itself may be used as the non-nucleophilic base. The amount of base charged to the reaction (or in the case of glycinamide, the excess over that to be reacted with the haloacetyl halide) should be at least about one equivalent per equivalent of haloacetyl halide charged.

Prior to and during the addition of haloacetyl halide, the system is preferably maintained at a temperature not greater than room temperature, more preferably 0-15° C., typically by use of an ice bath or refrigeration. After addition of the haloacetyl halide is complete, the temperature is allowed to rise to room temperature or somewhat above. At this point, a minor proportion of phase transfer catalyst optionally may be added to the reaction system, for example, between about 0.1% and about 3% by weight based on the amount of substituted or unsubstituted glycinamide in the charge. Preferably, however, the phase transfer catalyst is entirely omitted.

Thereafter caustic, preferably either NaOH or KOH, is added to the mixture to effect cyclization. Either powdered caustic or a 50% or greater aqueous solution may be used. Where powdered caustic is used, between about 1 and about 2 moles should be charged per mole of product. Where 50% caustic solution is used, at least about 4 moles should be charged. To complete the cyclization, the system is heated to a temperature between about 50° and about 150° C, preferably between about 75° and about 90° C., typically for one to three hours.

The product 2,5-diketopiperazine is conveniently recovered by simple phase separation, drying the organic phase (for example, over anhydrous magnesium sulfate) and stripping the solvent. Alternatively, and especially where an N,N'substituted 2,5-diketopiperazine is to be used in the synthesis of glyphosate or glyphosate precursors, the product can be subjected to further reaction after removal of the solvent. Thus, for example, the product may be converted to an N-substituted glycine or N-substituted glyphosate in accordance with the methods described in the copending applications of Miller and Taylor, Ser. No 778,818 filed Sept. 23, 1985, or Miller, Reitz and, Pulwer, Ser. No. 778,958, filed Sept 23, 1987.

Although particularly useful for the preparation of symmetrical 1,4-dialkyl-2,5-diketopiperazines for use in glyphosate synthesis, the process of the invention also affords an advantageous method for the preparation of specific asymmetric 1- and/or 4-substituted 2,5-diketopiperazines. Such can be prepared by selecting a glycinamide which initially contains the particular $R^1$ and $R^2$ substituents desired. Condensation of this glycinamide with haloacetyl halide and cyclization in the presence of alkali provides high conversion to the desired species. By contrast, synthesis from two different α-halocarboxamides, using the method of Okawara or Cavicchioni, produces a mixture of the desired asymmetric product with two by-products, one in which both nitrogens are substituted with $R^1$, and another in which both nitrogens are substituted with $R^2$. Furthermore, the present method also allows for the specific preparation of asymmetrically 3- and/or 4 substituted 2,5-diketopiperazines, which by prior art methods would provide unwanted mixtures of products as described above.

The following examples illustrate the invention.

EXAMPLE 1

Toluene (50 ml), N,N'-diisopropylglycinamide (3.69 g; 0.025 mol) and triethylamine (2.53 g; 0.025 mol) were charged to a 100 ml round bottom flask that was equipped with a magnetic stir bar and an addition funnel. The flask was cooled to 0°-5° C. in an ice bath and chloracetyl chloride (2.83 g; 0.025 mol) was added dropwise via the addition funnel. The mixture was then allowed to warm to room temperature and was stirred for about 30 minutes. The mixture was then filtered. The filtrates were combined and charged to a 500 ml Morton flask equipped with a thermometer, condenser and mechanical stirrer. Powdered sodium hydroxide (2.0 g; 0.050 mol) was charged to the flask and the reaction mixture was vigorously stirred and heated to 80° C. for one hour. The reaction mixture was then filtered and solvent removed under reduced pressure to give 4.68 g (94.4% yield) of 1,4-di-isopropylpiperazine-2,5-dione as an off-white solid. The solids were crystallized from ethanol to give a white, crystalline solid having a melting point of 177–180° C. Analytical results on the product were as follows:

$^1$H NMR (CDCl$_3$TMS, 90 MHZ), δ4.77 (Septet, J=7Hz,2H),
3.83 (S, 4H), 1.15 (d,J=7Hz12H), C$_{10}$H$_{18}$N$_2$O$_2$calc.,
C 60.58, H 9.15, N 14.13 (198.27) found 60.49, 9.16, 14.10 MS, m/e=198 (parent)

EXAMPLE 2

The compound N,N'-diisopropylglycinamide (16.6 g; 0.1 mole), methylene chloride (50 ml), and a 50% by weight sodium hydroxide solution (80 g) were charged to a flask and cooled in an ice bath. Chloracetyl chloride (11.2 g; 0.1 mole) was thereafter added dropwise and the reaction mixture was then allowed to come to room temperature. At this point, benzyltriethylammonium chloride (0.45 g) was added and the reaction mixture was stirred for 1.5 hours. The phases were separated, the organic phase was dried (over calcium chloride), and the volatiles were removed to leave 15.8 g (79.6% yield) of 1,4-diisopropylpiperazine-2,5-dione.

EXAMPLE 3

The compound N,N'-diisopropylglycinamide (7.91 g; 0.05 mole), toluene (70 ml), and triethylamine (5.06 g; 0.05 mole) were charged to a 500 ml Morton flask equipped with a mechanical stirrer, addition funnel and thermometer. The resulting mixture was cooled in an ice bath and chloracetyl chloride (5.65 g; 0.05 mole) was slowly added dropwise via the addition funnel. After addition of the chloractyl chloride was completed, the flask was allowed to warm to room temperature and stirred for one hour. The flask was then charged with six equivalents (12.0 g) of solid powdered sodium hydroxide. The addition funnel was replaced with a condenser, and the mixture was vigorously stirred and heated to 70° C. After the mixture has been stirred and heated for 1.5 hour, it was cooled and filtered. The collected solids were washed with methylene chloride. The filtrates and washings were combined and the solvent was removed under reduced pressure to give 8.99 g (90.7% of theoretical yield) of 1,4-diisopropylpiperazine-2,5-dione as a yellow-white solid.

EXAMPLE 4

The compound N,N-diisopropylglycinamide (7,91 g; 0.05 mole), triethylamine (5.06 g; 0.05 mole), and toluene (70 ml) were charged to a 500 ml Morton flask equipped with a mechanical stirrer and addition funnel. The mixture was cooled in an ice bath and chloracetyl chloride was slowly added dropwise to the stirred solution. Upon completion of the addition of the chloracetyl chloride, the ice bath was removed and the flask allowed to warm to room temperature and stirred for about 30 minutes. A precipitate was observed in the reaction flask. The flask was then charged with 50% by weight sodium hydroxide solution (24 g) and heated to 70° C. with vigorous stirring. After the mixture was heated and stirred for one hour, a sample was taken and analyzed by gas chromatography. The results showed 96.3% (area %) of N,N'-diisopropyl-2,5-diketopiperazine with virtually no remaining glycinamide (less then 2.7%).

The reaction mixture was worked up by adding methylene chloride (50 ml), separating the caustic layer, and washing the caustic layer with an additional aliquot of methylene chloride (1×25 ml). The organic layers were combined, washed with saturated NaCl solution, dried over anhydrous MgSO₄, filtered, and the solvent removed under reduced pressure to give 8.82 g (89%) yield of a pale, yellow white solid.

EXAMPLE 5

Toluene (70 ml), N-isopropyl-2-benzylaminoacetamide (4.12, 0.02 mole) and triethylamine (2.02 g, 0.02 mole) were charged to a 100 ml round bottom flask equipped with a magnetic stir bar and an addition funnel. The flask was cooled to 0°–5° C. in an ice bath and chloracetyl chloride (2.26 g, 0.02 mole) was added dropwise via the addition funnel. The mixture was then allowed to warm to room temperature and was stirred for 30 minutes. The mixture was then filtered. The filtrates were charged to a 500 ml Morton flask equipped with a thermometer, condenser and mechanical stirrer. Powdered sodium hydroxide (4.0 g, 0.10 mole) was charged to the flask and the mixture was vigorously stirred and heated to 70° C. for one hour. The mixture was filtered and solvent removed under reduced pressure to give 4.57 g (92.8%) of a tan solid. The solids were recrystallized from toluene to give a white, crystalline solid, melting point 106.5–107.5° C., identified as 1-isopropyl-4-benzylpiperazine-2,5-dione from the following analytical data:

NMR (CDCl₃, TMS, 90 MHz)δ6 7.30 (s, 5H), 4.78 (septet,

J=7Hz, 1H), 4.60 (s, 2H), 3.90 (s, 2H), 3.80 (s, 2H), 1.18 (d J=7Hz, 6H). Mass spectroscopy showed parent ion, m/e 246 and elemental analysis gave the following results:

|   | CALCULATED | FOUND |
|---|---|---|
| C | 68.27% | 68.33% |
| H | 7.37 | 7.38 |
| N | 11.37 | 11.33 |

EXAMPLE 6

Toluene (75 ml), N,N'-dibenzylglycinamide (6.36 g, 0.025 mole) and triethylamine (2.53 g, 0.025 mole) were charged to a 100 ml round bottom flask that was equipped with a magnetic stir bar and an addition funnel. The flask was cooled to 0°–5° C. in an ice bath and chloracetyl chloride (2.83 g, 0.025 mole) was added dropwise via the addition funnel. The mixture was then allowed to warm to room temperature and was stirred for 30 minutes. The mixture was then filtered. The filtrates were charged to a 500 ml Morton flask equipped with a thermometer, condenser and mechanical stirrer. Powdered sodium hydroxide (5.0 g, 0.125 mole) was charged to the flask and the mixture was vigorously stirred and heated to 70° C. for one hour. The mixture was then filtered and solvent removed under reduced pressure to give 6.69 g (91%) of a brown solid. The solids were recrystallized from chloroform to give a white, crystalline solid, melting point 173°–174.5° C., identified as 1,4-dibenzylpiperazine-2,-5-dione from the following analytical data; NMR (CDCl₃, TMS 90 MHz)δ7.25 (s, 10H), 4.54 (s, 4H), 3.85 (s, 4H). Mass spectroscopy showed parent ion, m/e 294, and elemental analysis gave the following results:

|   | CALCULATED | FOUND |
|---|---|---|
| C | 73.45% | 73.53% |
| H | 6.16 | 6.18 |
| N | 9.52 | 9.50 |

EXAMPLE 7

Toluene (50 ml), N,N'-diisopropylglycinamide (3.95 g, 0.025 mole) and triethylamine (2.53 g, 0.025 mole) were charged into a 100 ml round bottom flask that was equipped with a magnetic stir bar and an addition funnel. The flask was cooled to 0°–5° C. in an ice bath and 2-chloropropionyl chloride (3.17 g, 0.025 mole) was added dropwise via the addition funnel. The mixture was then allowed to warm to room temperature and was stirred for 30 minutes. The mixture was then filtered. The filtrates were combined and charged to a 500 ml Morton flask equipped with a thermometer, condenser and mechanical stirrer. Powdered sodium hydroxide (2.0 g, 0.05 mole) was charged to the flask and the mixture was vigorously stirred and heated to 80° C. for one hour. A sample of the mixture was analyzed by NMR and showed incomplete conversion to product. Fresh sodium hydroxide (2.0 g, 0.05 mole) was charged into the flask and heating and stirring was continued for an additional hour. NMR then showed complete conversion. The mixture was then filtered and solvent removed under reduced pressure to give 4.64 g. (87%) of a pale yellow-white solid. The solids were recrystallized from toluene to give a white solid, mp 160–163° C., identified as 1,4-diisopropyl3-methylpiperazine-2, 5-dione from the following analytical data:

NMR (CDCl₃, TMS, 360 MHz)δ4.72 (septet, J=7, 1 H), 4.52 (septet, J=7Hz, 1H), 4.00 (q, J=7Hz, 1H), 3.79 (s, 2H), 1.43 (d, J=7Hz, 3H), 1.24 (d, J=7Hz, 3H), 1.20 (d, J=7Hz, 3H), 1.14 (d, J=7Hz, 3H), 1.11 (d, J=7Hz, 3H). Mass spectroscopy showed parent ion, m/e 212 and elemental analysis gave the following results:

|   | CALCULATED | FOUND |
|---|---|---|
| C | 62.23% | 62.01% |
| H | 9.50 | 9.58 |
| N | 13.20 | 13.14 |

EXAMPLE 8

Toluene (50 ml), N-isopropyl-2-benzylaminopropionamide (5.51 g, 0.025 mole) and triethylamine (2.53 g, 0.025 mole) were charged to a 100 ml round-bottom flask equipped with a magnetic stir bar and an addition funnel. The flask was cooled to 0–5° C. in an ice bath and 2-chloro-2-phenylacetyl chloride (98%) (4.98 g, 0.025 mole) was added dropwise via the addition funnel. The flask was allowed to warm to room temperature and stirred for about 30 minutes. The mixture was then filtered. The filtrates were charged to a 500 ml Morton flask equipped with a thermometer, condenser and mechanical stirrer. Powdered sodium hydroxide (2.0 g, 0.05 mole) was charged to the flask and the mixture was vigorously stirred at 70°–80° C. for two hours. The mixture was then filtered and solvent removed under reduced pressure to give an orange-yellow oil, which was purified by chromatography on silica gel. Elution with 10% ethyl acetate-hexane gave 0.39 g (4.6%) of a yellow oil, identified as 1-isopropyl-3-methyl-4-benzyl-6-phenylpiperazine-2, 5-dione. Analytical data are presented below:

NMR (CDCl$_3$), TMS, 360 (MHz) δ7.34 (m, 10H), 4.97
(septet, J=7Hz, 1H), 4.54 (s, 1H), 3.77 (m, 2H), 3.54 (d, J=13Hz, 1H), 1.46 (d, J=7Hz, 3H), 1.42 (d, J=7Hz,
3H), 1.39 (d, J=7Hz, 3H); MS, m/e 336, 245, 132, 91.
Anal. calculated for C$_{21}$ H$_{24}$ N$_2$ O$_2$:

|   | CALCULATED | FOUND |
|---|---|---|
| C | 74.97 | 74.77 |
| H | 7.19 | 7.23 |
| N | 8.33 | 8.26 |

In view of the above, it will be seen that the several objects of the invention are achieved and other advantageous results attained.

As various changes could be made in the above methods without departing from the scope of the invention, it is intended that all matter contained in the above description or shown in the accompanying drawings shall be interpreted as illustrative and not in a limiting sense.

What is claimed is:

1. A process for the preparation of a substituted or unsubstituted 2,5-diketopiperazine represented by the formula:

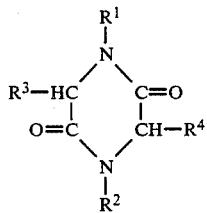

where R$^3$ and R$^4$ are independently selected from the group consisting of hydrogen, alkyl and aryl, and R$^1$ and R$^2$ are independently selected from the group consisting of hydrogen, alkyl having between 1 and about 12 carbon atoms, arylmethyl, aryl,

Y—CH$_2$—CH$_2$— and

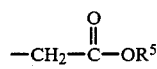

where Y is selected from the group consisting of

—OR$^5$,
—SR$^5$, and

and R$^5$ and R$^6$ are independently selected from the group consisting of alkyl having between 1 and about 6 carbon atoms; the process comprising bringing together under reaction conditions a substituted or unsubstituted glycinamide represented by the formula:

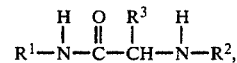

where R$^1$, R$^2$ and R$^3$ are as defined above, and a haloacetyl halide represented by the formula:

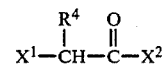

where X$^1$ and X$^2$ are halogen and R$^4$ is as defined above, and in the presence of a base forming said substituted or unsubstituted 2, 5-diketopiperazine.

2. A process as set forth in claim 1 wherein R$^1$ and R$^2$ are the same.

3. A process as set forth in claim 2 wherein R$^1$ and R$^2$ are alkyl.

4. A process as set forth in claim 3 wherein R$^1$ and R$^2$ are isopropyl.

5. A process as set forth in claim 2 wherein R$^1$ and R$^2$ are benzyl.

6. A process as set forth in claim 1 wherein said substituted or unsubstituted glycinamide and said haloacetyl halide are brought together in the presence of a hydrogen halide scavenger and thereafter, contacted with base to form said substituted or unsubstituted diketopiperazine.

7. A process as set forth in claim 6 wherein the hydrogen halide scavenger is a non-nucleophilic base.

8. A process as set forth in claim 7 wherein said non-nucleophilic base comprises a non-nucleophilic organic amine.

9. A process as set forth in claim 8 wherein said non-nucleophilic organic amine is selected from the group consisting of triethylamine and pyridine.

10. A process as set forth in claim 8 wherein the non-nucleophilic organic amine is a stoichiometric excess of the substituted or unsubstituted glycinamide with respect to the amount of haloacetyl halide present.

11. A process as set forth in claim 8 wherein the haloacetyl halide is added slowly to a solution comprising said substituted or unsubstituted glycinamide and said non-nucleophilic organic amine, and thereafter, caustic selected from the group consisting of sodium hydroxide and potassium hydroxide is added to the solution to form the diketopiperazine.

12. A process as set forth in claim 11 wherein said caustic comprises a powdered alkali metal hydroxide and is added in a proportion of between about 1 and about 2 moles per mole of haloacetyl halide charged.

13. A process as set forth in claim 11 wherein said caustic comprises an aqueous solution containing at least about 50% by weight of an alkali metal hydroxide and is added in a proportion of at least about 4 moles per mole of haloacetyl halide.

14. A process as set forth in claim 11 wherein said solvent comprises an organic solvent which is not reactive with haloacetyl halide.

15. A process as set forth in claim 14 wherein said solvent is selected from the group consisting of toluene and xylene.

16. A process as set forth in claim 11 wherein the diketopiperazine is formed at a temperature of between about 50° and about 150° C.

17. A process as set forth in claim 1 wherein said haloacetyl halide is represented by the formula:

$$X^{1'}-CH_2-CO-X^{2'}$$

wherein $X^{1'}$ and $X^{2'}$ are independently selected from the group consisting of chlorine and bromine.

18. A process as set forth in claim 17 wherein said haloacetyl halide is chloracetyl chloride.

19. A process as set forth in claim 18 wherein $R^1$ and $R^2$ are isopropyl.

20. A process as set forth in claim 18 wherein $R^1$ and $R^2$ are benzyl.

* * * * *

UNITED STATES PATENT AND TRADEMARK OFFICE
CERTIFICATE OF CORRECTION

PATENT NO. : 4,694,081
DATED : September 15, 1987
INVENTOR(S) : William H. Miller and William D. Taylor It is certified that error appears in the above-identified patent and that said Letters Patent are hereby corrected as shown below:

Column 1, line 21, the word --and-- should be between "1985" and "Miller".

Column 2, line 43, the following formula should be above the other formula as follows:

-- $Y-CH_2-CH_2-$ and --

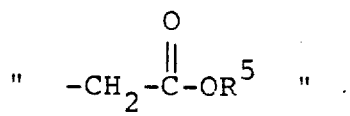

" $-CH_2-\overset{\overset{O}{\|}}{C}-OR^5$ " .

Column 2, line 50, " $-OR^5$, " should be -- $-SR^5$, --.

Column 3, line 68, " $R^6$ " should be -- $R^5$ --

Column 6, line 12, " (16.6 g; " should be -- (15.6 g; --

Signed and Sealed this

Ninth Day of February, 1988

Attest:

DONALD J. QUIGG

Attesting Officer   Commissioner of Patents and Trademarks